United States Patent
Karavas et al.

(10) Patent No.: US 9,943,484 B2
(45) Date of Patent: Apr. 17, 2018

(54) PREPARATION OF POLYLACTIDE-POLYGLYCOLIDE MICROPARTICLES HAVING A SIGMOIDAL RELEASE PROFILE

(71) Applicant: PHARMATHEN S.A., Pallini Attikis (GR)

(72) Inventors: Evangelos Karavas, Pallini Attikis (GR); Efthymios Koutris, Pallini Attikis (GR); Sotiria Haitidou, Pallini Attikis (GR); Theofanis Mantourlias, Pallini Attikis (GR); Georgia Papanikolaou, Pallini Attikis (GR)

(73) Assignee: PHARMATHEN S.A., Pallini-Attikis (GR)

( * ) Notice: Subject to any disclaimer, the term of this patent is extended or adjusted under 35 U.S.C. 154(b) by 0 days.

(21) Appl. No.: 14/898,415

(22) PCT Filed: Jun. 18, 2014

(86) PCT No.: PCT/EP2014/001652
§ 371 (c)(1),
(2) Date: Dec. 14, 2015

(87) PCT Pub. No.: WO2014/202214
PCT Pub. Date: Dec. 24, 2014

(65) Prior Publication Data
US 2016/0143851 A1    May 26, 2016

(30) Foreign Application Priority Data
Jun. 20, 2013    (WO) .................. PCT/EP2013/001821

(51) Int. Cl.
| | |
|---|---|
| *A61K 9/14* | (2006.01) |
| *A61K 9/16* | (2006.01) |
| *C08J 3/12* | (2006.01) |
| *C08J 3/14* | (2006.01) |
| *A61K 31/519* | (2006.01) |

(52) U.S. Cl.
CPC .......... *A61K 9/1682* (2013.01); *A61K 9/1647* (2013.01); *A61K 9/1694* (2013.01); *A61K 31/519* (2013.01); *C08J 3/12* (2013.01); *C08J 3/14* (2013.01); *C08J 2300/16* (2013.01); *C08J 2367/04* (2013.01)

(58) Field of Classification Search
None
See application file for complete search history.

(56) References Cited

U.S. PATENT DOCUMENTS

| | | | |
|---|---|---|---|
| 5,288,496 A | 2/1994 | Lewis | |
| 5,792,477 A * | 8/1998 | Rickey | ................. A61K 9/1647 264/4.1 |

FOREIGN PATENT DOCUMENTS

WO        00/40221 A1     7/2000

* cited by examiner

*Primary Examiner* — Jessica Worsham
(74) *Attorney, Agent, or Firm* — AKC PATENTS, LLC

(57) ABSTRACT

The present invention relates to preparation of biodegradable microparticles formed from polylactide-polyglycolide copolymers (PLGA) polymer and how to achieve sigmoidal release of active pharmaceutical compound from the microparticles. In particular, the present invention relates to emulsification of an inner/oil phase to an outer/water phase followed by quenching and a single drying step for the preparation of microparticles having a preferred release profile of preferably basic/nucleophilic compounds such as risperidone. Alternatively the present invention is also suitable for hydrophobic compounds that have poor water-solubility and a high drug loading of >20% w/w is required. The release profile can be controlled by adjusting the degree of saturation of the outer/water phase with the organic solvent used in the inner/oil phase, the polymer concentration of the inner/oil phase and the temperature at the quenching step. In particular, an initial lag phase and a substantially sigmoidal release profile are achieved by using an outer aqueous phase over saturated with the solvent used in the inner phase at emulsification step, in combination with a low temperature during quenching.

9 Claims, 3 Drawing Sheets

PREPARATION OF POLYLACTIDE-POLYGLYCOLIDE MICROPARTICLES HAVING A SIGMOIDAL RELEASE PROFILE

TECHNICAL FIELD OF THE INVENTION

The present invention relates to preparation of biodegradable microparticles formed from poly(D,L lactide-co-glycolide) (PLGA) polymer and how to achieve sigmoidal release of active pharmaceutical compounds from the microparticles. In particular, the present invention relates to emulsification of an inner/oil phase to an outer/water phase followed by quenching and a single drying step for the preparation of microparticles having a preferred release profile of, preferably basic/nucleophilic compounds such as risperidone. Alternatively the present invention is also suitable for hydrophobic compounds that have poor water-solubility and a high drug loading of >20% w/w is required. The release profile can be controlled by adjusting the degree of saturation of the outer/water phase with the organic solvent used in the inner/oil phase, and the temperature at the quenching step. In particular, an initial lag phase and a substantially sigmoidal release profile are achieved by using an outer aqueous phase oversaturated with the solvent used in the inner phase at emulsification step, in combination with a low temperature during quenching.

BACKGROUND OF THE INVENTION

Despite the literature focusing on the considerable challenges with injectable depots for biomacromolecules, hydrophobic compounds are an extremely significant class of drug substances and pose unique challenges in their own right. It is estimated that up to 40% of all new chemical entities show poor solubility. The term "hydrophobic compound" roughly describes a heterogeneous group of small molecules (less than 1300) that exhibit poor solubility in water but that are typically, but certainly not always, soluble in various organic solvents. Often, the terms slightly soluble (1-10 mg/ml), very slightly soluble (0.1-1 mg/ml), and practically insoluble (<0.1 mg/ml) are used to categorize such compounds. Additionally "basic compound" means that when the compound is dissolved in water it gives a solution with hydrogen ion activity greater than that of pure water and a pH of more than 7.0. The basic compound may also be a hydrophobic compound.

Controlled-release dosage forms improve the effectiveness of drug therapy by increasing the therapeutic activity while reducing the intensity of side effects and number of drug administration required during treatment. For certain drugs that (i) have a broad therapeutic window, (ii) require a low daily dose, and (iii) are going to be used for the long-term treatment of disease, injectable controlled release depots such as drug-loaded biodegradable polymer microparticles, may provide such an alternative delivery strategy, potentially rescuing an otherwise undeliverable drug.

Biodegradable microparticles (microcapsules and microspheres) ranging in diameter from about 10 to 125 μm can serve satisfactorily as prolonged-release drug-delivery systems. Microparticles comprised of certain therapeutic agents and suitable biodegradable matrices may be suspended in a viscous diluent and injected intramuscularly (IM) or subcutaneously.

A variety of biodegradable polymers have been used for the controlled release of different drugs. The selection and design of a suitable biodegradable polymer is the first challenging step for the development of a parenteral drug delivery system. Several classes of synthetic polymers have been proposed, which include poly(ester)s, poly(anhydride)s, poly (carbonate)s, poly(amino acid)s, poly(amide)s, poly (urethane)s, poly(ortho-ester)s, poly(iminocarbonate)s, and poly(phosphazene)s.

A variety of methods is known by which hydrophobic compounds can be encapsulated in the form of microparticles(Christian Wischke and Steven P. Schwendeman, "Principles of encapsulating hydrophobic compounds in PLA/PLGA microparticles", International Journal of Pharmaceutics 364 (2008) 298-327). The most well-established are summarized below:

o/w Emulsion Technique (Solvent Evaporation and/or Extraction)

As a considerable number of hydrophobic compounds are soluble in various water-immiscible organic solvents and, of course, are poorly soluble in water, one of the simplest methods to encapsulate such drugs in biodegradable polymers is by the oil-in-water (o/w) emulsion/solvent evaporation and or extraction technique. The o/w process involves dissolving the polymer (in the most of the cases PLGA) in a water immiscible, volatile organic solvent (such as dichloromethane (DCM), tetrahydrofuran (THF) and ethyl acetate) and then dissolving the compound in the prepared solution or alternative dissolving the compound in a miscible co-solvent and mixing. Co-solvents are generally used for drugs that do not show a high solubility in the primary organic solvent. The resulting organic oil phase is then emulsified in an aqueous solution (continuous phase) containing an appropriate emulsifier. The emulsifiers included in the aqueous phase act as stabilizers for the oil-in-water emulsion. The emulsion is then subjected to solvent removal by either evaporation or extraction process to solidify the oil droplets. In general, volatile solvents can be removed from such emulsions by evaporation to a gas phase or in any case by extraction to the continuous phase. In the former case, the emulsion is maintained at reduced pressure or at atmospheric pressure and the stir rate is reduced while the temperature is increased to enable the volatile solvent to evaporate. In the latter case, the emulsion is transferred to a large quantity of water (with or without surfactant) or other quench medium, into which the solvent associated with the oil droplets is diffused out. Combination of solvent evaporation and extraction is also applicable. The solid microspheres so obtained are then washed and collected by sieving. These are then dried under appropriate condition such as vacuum drying or lyophilized.

s/o/w Emulsion Technique

This technique is usually used when drug cannot be dissolved in a carrier solvent or solvent mixture or extensive drug loss to the continuous phase cannot be avoided when employing cosolvent systems. In this method the drug substance is dispersed in the oil phase consisting of the organic solvent or mixture of solvents and the polymer dissolved into this phase. Due to a low but distinct solubility of certain active agents in the organic solvent, a certain portion of the drug might also be in solution in s/o/w formulations. The s/o/w method requires a very low drug particle size in order to allow a complete encapsulation of the drug crystals. Besides the necessity of small-sized drug material, other drawbacks of the s/o/w technique might be the tendency of the drug to show sedimentation (higher density than suspension medium) or flotation (caused by adhesion of gas bubbles to the hydrophobic surface due to low wettability) during the encapsulation process and, in the later stages of the product development, difficulties can also be expected during scaling up to large-scale manufacture. Alterations, which might result from changes in the drug synthesis, e.g., in the drug crystal structure or the wetting behavior, are expected to affect the release profile from s/o/w particles. Moreover, differences in the release might appear compared to dense microspheres that were prepared by the o/w technique and show a homogeneous drug distribution.

o/o Method

Although being classified as hydrophobic compounds, some active substances exhibit an appreciable solubility in aqueous media like the external water phases. Therefore, o/w methods are expected to result in low encapsulation efficiencies due to a flux of the active agent from the dispersed phase to the larger volume of the continuous phase during the encapsulation process. In order to overcome this issue, o1/o2 emulsion methods can be used. The drug substance and the polymer are dissolved in an organic solvent (e.g., acetonitrile) and then the solution is emulsified into a continuous phase consisting of a solution of an emulsifier (HLB typically <8) in oil, e.g., cottonseed oil or mineral oil. The o1-phase solvent (i.e., acetonitrile) is extracted in the external oil phase (acetonitrile solubility in cottonseed oil 10%) which should be a non-solvent for both the polymer and the drug. Alternative methods concern the s/o/o technique combining the concepts of s/o/w and o/o methodologies. However, for methods carried out in oil the removal of the continuous phase requires a special treatment, e.g., washing of the particles with hexane or petroleum ether. The emulsification process can be achieved by the mechanical stirring, high shear mixers and/or static mixers.

Spray Drying

Microparticles are obtained by spraying a solution or suspension of a drug in an organic solution of the polymer. Spray drying is defined as the transformation of a feed from a fluid state (solution, or dispersion) into a dried particulate form by spraying the feed into a hot gaseous drying medium (e.g., hot air). It is a continuous one-step processing operation in which four different phases can be distinguished, namely: atomization of the feed, mixing of spray and air, solvent evaporation, and product separation. A variety of atomization systems are available, which may be classified according to the nozzle design as rotary atomization, pressure atomization, and two-fluid atomization. Spray drying technique can overcome the issue of large volumes of solvent-contaminated water phase that result from emulsion-based encapsulation methods, however it faces scalability issues related to technology transfer from small to large scale production.

There is a substantial body of evidence supporting the hypothesis that the release of drug from sustained release parenteral systems is predominately controlled by the characteristics of the delivery system and dependent mainly on a combination of diffusion (early phase) and hydrolytic erosion (later phase) (Cheng-ju Kim, Controlled Release Dosage Form Design, TECHNOMIC publications; Xiaoling Li, Bhaskara R. Jasti, Design of Controlled Release Drug Delivery Systems, McGraw-Hill). Release profiles are typically illustrated as the cumulative release, expressed as a percentage of the total amount of active agent present in the microparticles, as a function of time. Different clinical applications, and/or different active agents, may require different types of release profiles. For example, one type of release profile includes a substantially linear release profile over time. Another type of release profile is a sigmoidal release profile characterized by an initial lag phase, a steep intermediate release phase, and a flat final release phase.

The drug release mechanism form PLGA microparticles has been found to be a combination of polymer erosion and drug diffusion (N. Faisant et al., "PLGA-based microparticles: elucidation of mechanism and a new, simple mathematical model quantifying drug release", Eur. J. Pharm. Aci., 15 (2002) 355-366). One critical variable that affects the release profile of the biodegradable microparticle product is the molecular weight of the polymer or polymeric matrix material in the final microparticle product. The molecular weight of a polymer influences the biodegradation rate of the polymer. For a diffusional mechanism of active agent release (diffusion-controlled), the polymer should remain intact until the entire active agent is released from the microparticles, and then degrade. The active agent can also be released from the microparticles as the polymeric matrix material bioerodes (degradation-controlled). By an appropriate selection of polymeric materials a microparticle formulation can be made in which the resulting microparticles exhibit both diffusional release and biodegradation release properties.

Drug release from biodegradable PLGA microparticles of particle size >10 µm is controlled by matrix/bulk-erosion and these systems are selected when sigmoidal release profiles are required (M. Körber, "PLGA Erosion: Solubility- or Diffusion-Controlled?", Pharm Res (2010) 27:2414-2420). The polymer chain of water-insoluble polymer is broken down to smaller, water soluble molecules by hydrolysis of labile ester bonds in the polymer backbone. Then drug dispersed physically in the interstices of the polymer matrix releases. The by-products of the polymer degradation are lactic and glycolic acids, which are commonly found in metabolic cycles in the body. The drug release is expected to begin after a lag time when the polymer Mw falls below a critical value where mass loss can take place. Different polymer types are known to require different times for complete degradation, with larger molecular weight and particularly higher lactide content, and, in the case of l- or d-PLA, crystalline instead of amorphous structures, resulting in a slower degradation and an expected slower release. In general, drug release from a matrix-controlled system does not furnish zero-order kinetics unless intricate fabrication processes used in manufacturing (e.g. ununiformed concentration distribution, modification of geometry, etc).

Unexpected early and/or almost linear release profiles form PLGA microparticles have been observed for basic/nucleophilic drug substances (e.g., compound carrying tertiary amino groups) (H. V. Maulding et al., "Biodegradable microcapsules: acceleration of polymeric excipient hydrolytic rate by incorporation of a basic medicament", Journal of Controlled Release 3 (1986) 103-117; Y. Chsn and C. G. Pitt, "The acceleration of degradation-controlled drug delivery form polyester microspheres", Journal of Controlled Release 8 (1989) 259-265;). The very rapid drug release (observed both in vitro and in vivo) is attributed to the acceleration of the hydrolytic degradation of the polymer matrix (hydrolytic cleavage of the polymer chain ester bonds) caused by the basic drug substances (base catalyzed hydrolysis). Examples of such drug substances that induce the hydrolysis of the PLGA polymers include but not limited to thioridazine hydrochloride, ketotifen, cinnarizine, indenorol, clonidine, naltrexone, merepidine, methadone, promethazine and risperidone. It was proved that the steric accessibility of the unsolvated amine nitrogen of the compound defined its catalytic effectiveness and the degree of acceleration of polymer chain scission was proportional to the initial concentration of the base (% drug loading) into the polymer matrix. In particular, thioridazine HCl was incorporated into PLGA microspheres resulting in almost immediate release occurring both in vitro and in vivo contrary to the results expected with a polymer as PLGA which degrades in about one year and releases drugs over weeks to months. Another amine, ketotifen, was employed in making microspheres with PLGA and analogous in vitro release results were observed. Accelerated degradation rates related to rapid release were also observed for microparticles containing meredipine, methadone and promethazine.

Another active compound inducing hydrolysis of polyesters backbones such as PLGA polymers is Risperidone. Risperidone (also known as 4-[2-[4-(6-fluorobenzo[d]isoxazol-3-yl)-I-piperidyl]ethyl]-3-methyl-2,6-diazabicyclo [4.4.0]deca-1,3-dien-5-one and marketed under the trade name RISPERDAL®) is an atypical antipsychotic medication indicated for the treatment of schizophrenia. Risperidone product is also available in the market as sustained release parenteral depot under the trade name RISPERDAL CONSTA. Risperdal consta product consists of a vial containing the microspheres for depot suspension and a prefilled syringe containing a suitable solvent for suspension. The solid powder of microparticles is mixed with diluent to become a suspension that is given every-two week intramuscularly. The in vivo release profile of Risperdal consta is as follows: classical tri-phasic release pattern with a low burst effect ($\leq$3.5%), a latent period of 4 weeks with no release, and the preponderant drug release between weeks 4-6.

Degradation studies of PLGA microparticles containing risperidone compared to placebo microparticles (without risperidone) revealed that the presence of risperidone accelerates the degradation rate of PLGA polymers (F. Selmin, P. Blasi and P. P. DeLuca, "Accelerated Polymer Biodegradation of Risperidone Poly(D, L-Lactide-Co-Glycolide) Microspheres, AAPS PharmSciTech, Vol. 13, No. 4 (2012) 1465-1472). The hydrolytic effect of risperidone was also observed during the preparation of microparticles when risperidone and PLGA polymer are co-dissolved in organic solvent to prepare oil phase to be emulsified in the aqueous continuous phase. Patent EP1282404 provides a method for the control of the molecular weight of a polymer forming microparticles containing a nucleophilic compound by adjusting hold time and temperature of the nucleophilic compound/polymer solution during the manufacturing process. The acceleration of the polymeric matrix of microparticles by the presence of risperidone substance results in rapid drug release and often in undesired linear release profiles.

Thus, there is a need in the art for an improved method for controlling the release profile in the finished microparticle product containing basic/nucleophilic compounds such as risperidone. Alternatively the present invention is also suitable for hydrophobic compounds that have poor water-solubility and a high drug loading of >20% w/w is required. Patent EP-B-1140029 claims a method for the preparation of PLGA microparticles containing risperidone with "s"-shaped release profile by adjusting the degree of drying that is performed during the preparation of the microparticles. In particular, the patent discloses that additional intermediate drying steps of the particles can provide sigmoidal release profile. This method however increases the number of the processing steps and complicates manufacturing and increase risks when microparticle products are intended for human use and production should take place under aseptic conditions.

SUMMARY OF THE INVENTION

The present invention relates to preparation of biodegradable polymeric microparticles that exhibit desired release profiles of basic/nucleophilic active pharmaceutical compound that tends to accelerate the degradation rate of polymer matrix causing uncontrolled early and/or linear drug release. Alternatively the present invention is also suitable for hydrophobic compounds that have poor water-solubility and a high drug loading of >20% w/w is required. More particularly, the present invention relates to preparation of PLGA microparticles containing basic/nucleophilic compounds, such as risperidone, that follow a sigmoidal release profile characterized by an initial lag phase, a steep intermediate release phase, and a flat final release phase. In a further aspect, present invention relates to preparation of basic/nucleophilic compound, such as risperidone, loaded microparticles that release less than 10% of drug substance in 20 days, 50% within day 30 and day 35 and more than 80% up to day 40 when dissolution is performed at 37° C. (normal conditions).

In one aspect, the present invention relates to simple process for making microparticles involving oil-in-water (o/w) emulsification solvent extraction and/or solvent evaporation followed by a single drying step. In a further aspect we present a process for the preparation of biodegradable microparticles of PLGA polymer, having a sigmoidal release profile of a basic compound, or for a hydrophobic compound that has poor water-solubility, contained within the microparticles, comprising preparing an oil-in-water emulsion wherein the oil phase comprises PLGA, the compound and an organic solvent and the water phase comprises water, surfactant, optionally a buffer, and the same organic solvent as in the oil phase, and then performing a solvent extraction/evaporation step of the emulsion, followed by a single drying step of the hardened microparticles.

Preferably the buffer is selected from; phosphate, citrate, acetate and tris-buffers. Ideally the pH of the buffer is adjusted to a value where the compound has lower solubility. By controlling the pH any leakage of the compound to the outer phase during emulsification and/solvent extraction and evaporation process during the quench step is minimized.

By the use of the term "single drying step" we mean that only one drying step is required in order to achieve the benefits of the invention and that addition washing and drying steps are not required.

More particularly a process for the preparation of PLGA microparticles containing at least one basic/nucleophilic compound, such as risperidone, or for a hydrophobic compound that has poor water-solubility, comprising:
i. preparing an inner oil phase by dissolving the PLGA polymer and compound in an organic solvent; the polymer concentration in the organic solvent is as high as 5-40% wt. and polymer solution appears a viscosity of 10-1000 cP, preferably 10-200 cP,
ii. preparing an outer aqueous phase consisting of polyvinyl alcohol (PVA) solution in water, optionally with an aqueous buffer solution and the pH adjusted to a value that drug substance appears the lower solubility and the organic solvent used in oil phase,
iii. emulsifying the inner phase into the outer phase either by mechanical stirring or using a high shear homogenizer,
iv. transferring the emulsion into a temperature set and thermostatically controlled quench media, and preferably with the volume of the quench media controlled from 0.7 to 3 times (preferably 1) of the volume needed to dissolve all of organic solvent out of the emulsion oily microdroplets,
v. separating the resulting hardened microparticles and, optionally washing of the microparticles, and
vi. drying the microparticles in a single drying step, preferably by vacuum drying, with no further washing and/or drying step.

By adjusting the process parameters of the manufacturing method the release profile can be controlled. In one aspect, the critical process parameters to achieve the desired release profile include:
- degree of saturation of the outer/aqueous phase with the organic solvent used in the inner/oil phase
- polymer concentration of inner/oil phase
- temperature at the quenching step More particularly, an initial lag phase and a substantially sigmoidal release profile of risperidone are achieved by:
- using an outer phase over saturated with the organic solvent used in the inner/oil phase at emulsification step and performing the quench step at low temperature (preferably the temperature is between 5° C. to 15° C.) or
- using an outer phase oversaturated with the organic solvent used in the inner/oil phase at emulsification step and performing the quench step at high temperature or
- using an inner/oil phase with a low polymer concentration and an outer phase saturated with the organic solvent used in the inner/oil phase at emulsification step and performing the quench step at low temperature Accordingly, the present invention relates to preparation of microparticles with sigmoidal release of risperidone by:
- using an outer phase that contains organic solvent 2 to 10 times above the saturation point and performing quench at a temperature as low as 5° C. or less, or
- using an outer phase that contains organic solvent 2 to 10 times above the saturation point and performing quench at a higher temperature between 30° C. to 40° C.
- using an inner/oil phase with low polymer concentration (preferably below 10% wt.) and an outer phase saturated with the organic solvent and performing quench at a temperature as low as 5° C. or less.

Preferably the organic solvent of the outer aqueous phase is the same as that used in the inner oil phase. Additionally the solvent is added to the outer phase prior to emulsification. Preferred solvents to be used in the inner aqueous phase are selected from one or more of the following; ethylacetate, tetrahydrofurane, acetonitrile, dichloromethane, hexafluoroisopropanol, chloroform and acetone. More preferably, in the present invention dichloromethane is used.

A feature of the present invention is that it provides microparticles that release risperidone active substance in a controlled manner. In particular, the present invention advantageously provides microparticles containing risperidone that release risperidone following a sigmoidal release pattern. An advantage of the present invention is that a limited number of processing steps is needed. Limiting of processing steps is essential for aseptic preparations such as sustained release parenteral depots for human use.

DETAILED DESCRIPTION OF THE INVENTION

The present invention is directed to risperidone controlled release delivery system. Risperidone (also known as 4-[2-[4-(6-fluorobenzo[dJisoxazol-3-yl)-I-piperidyl]ethyl]-3-methyl-2,6-diazabicyclo[4.4.0]deca-1,3-dien-5-one) is an atypical antipsychotic medication indicated for the treatment of schizophrenia. The chemical structure of risperidone is shown below:

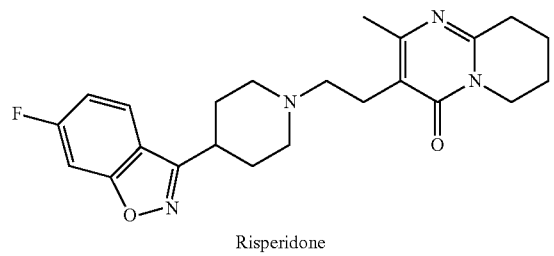 [SMILES: Cc1nc2n(c(=O)c1CCN1CCC(c3noc4cc(F)ccc34)CC1)CCCC2]

Risperidone

However, the process of present invention, with possible minor modifications within the knowledge of the person skilled in the art, could find application in other active pharmaceutical agent formulated as controlled delivery system. Such an example is Ocreotide, which is a natural octapeptide that mimics natural somatostatin pharmacologically.

The delivery system refers to biodegradable microparticles consisting of PLGA polymer as matrix forming material. Suitable commercially obtainable polymers for use according to the present invention include but not limited to RESOMER® and LAKESHORE BIOMATERIALS by Evonik Industries AG, LACTEL® by Durect Corp., PURASORB® by PURAC Biochem BV. The PLGA polymers used in the present invention may have a ratio of lactic acid and glycolic acid in the range of about 50:50 to about 85:15 and a weight average molecular weight (Mw) in the range of 20,000 to 400,000. Preferably the present invention uses PLGA having a monomer ratio of 75:25 and a weight average molecular weight in the range of 60,000 to 250,000.

The term microparticles refer to particle size of 10-250 μm, most preferably in the range of 20-150 μm. The measurement is the D4,3 value (volume based mean diameter—as measured by laser light scattering—using a suitable dispersant).

The controlled release characteristics refer to sigmoidal release profile characterized by an initial lag phase, a steep intermediate release phase and a flat final release rate. In particular, the experimentally measured release profile of produced microparticles appears a substantial "S" shape and can be fitted satisfactorily the following equation:

$$\% \text{ Release} = y_o + \frac{a}{1 + \exp\left(\frac{-(x - x_0)}{b}\right)}$$

The release profile refers to the quantity or amount of active agents that is released from the microparticles as a function of time measured by an in vitro method with in vivo relevance. One type of in vitro release method that simulates in vivo conditions is dissolution testing at 37° C. and pH value of 7.4.

Figure 1:
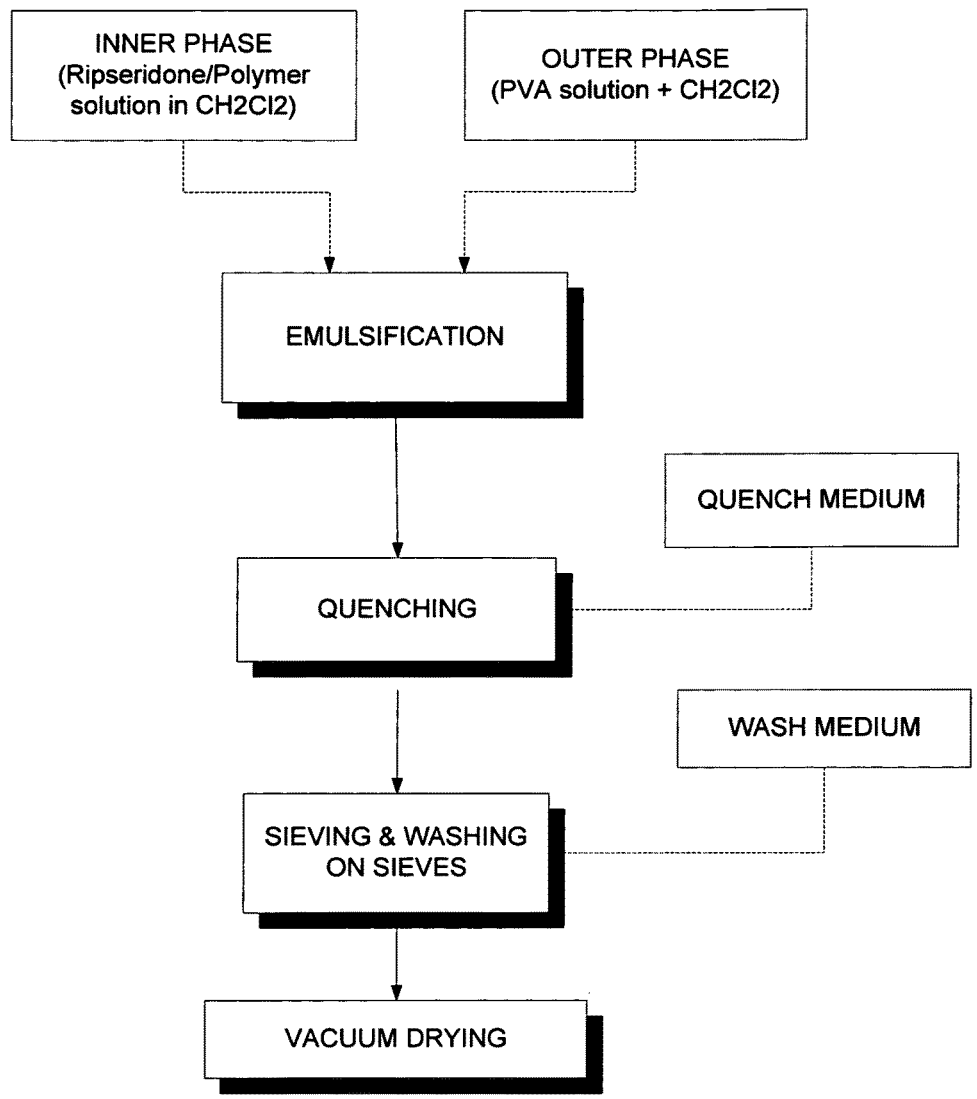
FIG. 1 illustrates the manufacturing process
Figure 2:
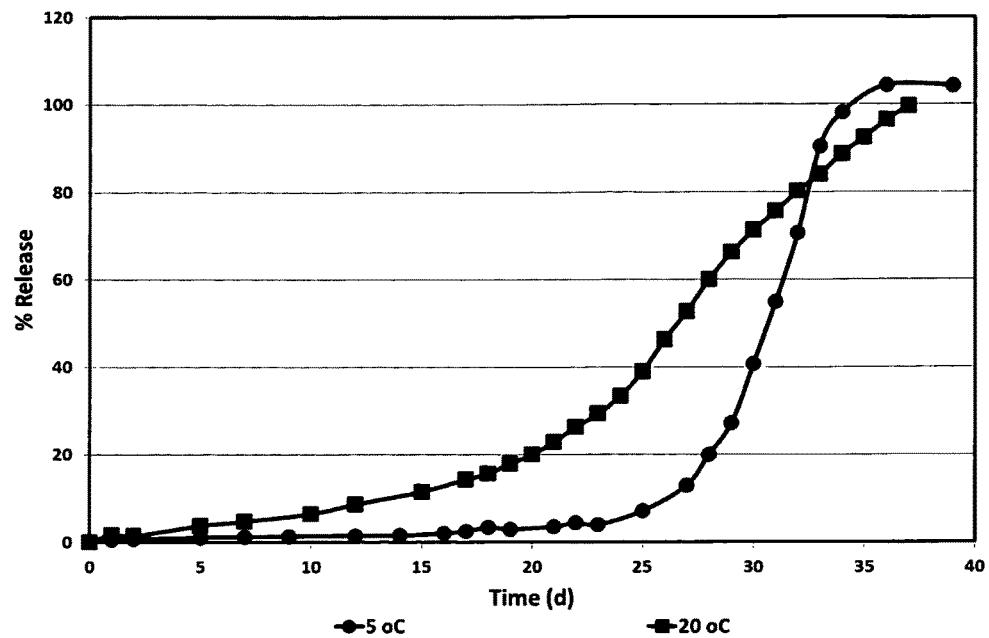
FIG. 2 illustrates in vitro release profiles of preparations 1a and 1b
Figure 3:
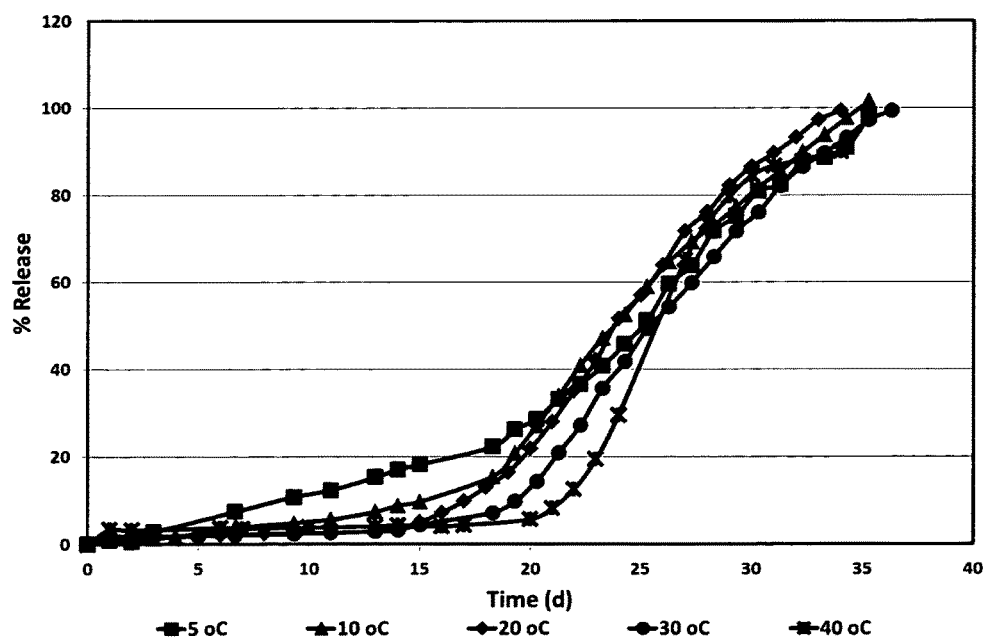
FIG. 3 illustrates in vitro release profiles of preparations 2a-2e
Figure 4:
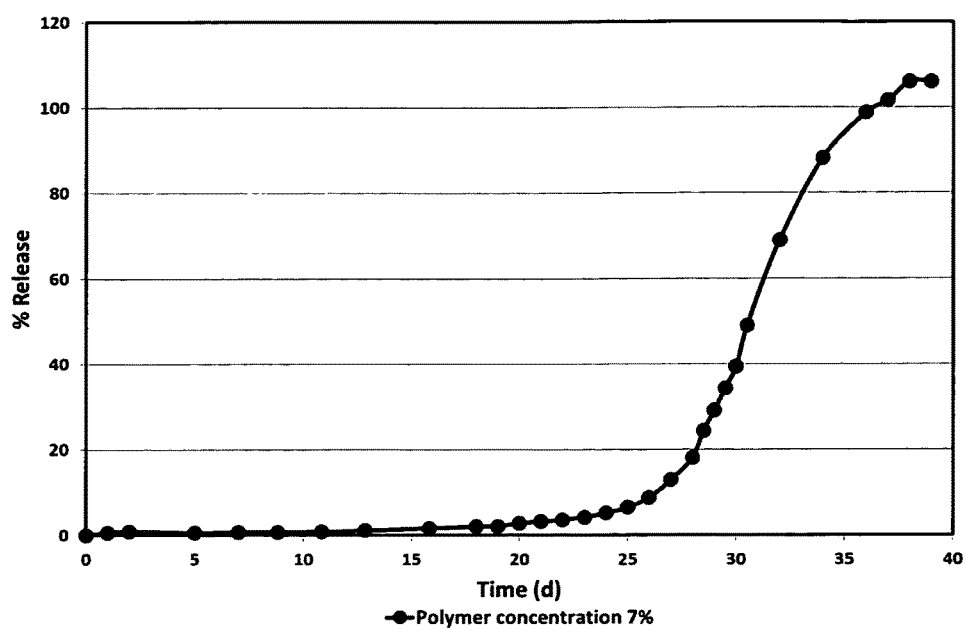
FIG. 4 illustrates in vitro release profile of preparation 3

Risperidone loaded microparticles were manufactured by a simple emulsification solvent evaporation and/or extraction technique followed by a single drying step and the desired dissolution profile was achieved by adjusting the manufacturing parameters. A schematic depiction of the manufacturing process is provided in FIG. 1.

According to the proposed method, PLGA polymer is dissolved in a volatile organic solvent with low water miscibility and the risperidone is then dissolved in the polymer solution. Organic solvents that can be used in the present invention include but not limited to ethylacetate, tetrahydrofurane, acetonitrile, dichloromethane, hexafluoroisopropanol, chloroform and acetone. More preferably, in the present invention dichloromethane is used.

This mixture is then emulsified in an outer phase containing a surfactant, especially preferred is polyvinyl alcohol (PVA), resulting in an oil-in-water (o/w) emulsion. Examples of other surfactants that optionally can be employed include one or more; anionic surfactants (such as, sodium oleate, sodium stearate or sodium lauryl sulfate), non-ionic surfactants (such as Poloxamers, Tweens), polyvinylpyrrolidone, carboxymethyl cellulose sodium and gelatin, used independently or in combination. Polyvinyl alcohol (PVA), preferably have a weight average molecular weight from about 10,000 to about 150,000 Da that correspond to viscosity range of 3-9 cP when measured as a 4% aqueous solution at 200 C, 85-89% degree of hydrolysis and ester number of 130-150. Selected PVA grades that are used in the present invention include Emprove PVA 4-88 (Mw 25,000-30,000; viscosity 4% in water: 3.4-4.6 cPs), PVA 8-88 (Mw about 65,000; viscosity 4% in water 6.8-9.2 cPs) and PVA 18-88 (Mw about 130,000; viscosity 4% in water) available by MerckKGaA. Amount of the surfactant added to the aqueous phase is preferably up to 5.0% (w/w) relative to mass of the aqueous solution. More preferably the amount of surfactant (optimally the PVA amount) is from about 0.5 to about 2.5% w/w.

In the present invention, apart from the surfactant, the outer phase also contains an amount of the organic solvent as used in the preparation of the inner phase (preferably dichloromethane). The amount of organic solvent added is sufficient to result either in the saturation of the surfactant solution (i.e., water solubility of dichloromethane is 1.3-1.8% w/w) or in the formation of a separate phase (oversaturation). In the latter case the amount of the solvent added in the outer phase is 2-10 times above the saturation point (meaning 2-10 times the amount of the solvent that can be dissolved in the volume of the aqueous phase), more preferably 4-6 times above the saturation point of the surfactant solution (inclusive of the buffer if present). Equivalent to the oversaturation of the outer phase with the solvent present used in the inner/oil phase, is the preparation of an inner/oil phase with a low polymer concentration (below 10% wt.).

In particular, either oversaturation of the outer phase or preparation of an inner/oil phase with low polymer concentration results in the formation of risperidone loaded microparticles having a desired distribution of the risperidone drug substance in the polymer matrix. In the present case the desired drug distribution is referred to drug substance that is not located close to the surface of the polymer microparticle. More specific, microparticles of the present invention have an enriched to drug substance core in contrast to an API-depleted region near the surface. The surface of the microparticles lacks of drug substance of any form (crystalline or amorphous. Depletion of the API from the surface of the particles is experimentally assessed by ATR analysis.

In the present invention the emulsification of the inner phase in the outer phase can be performed with one of the following means: i) mechanical stirring, ii) batch homogenizer iii) in line homogenizer. Preferably, the emulsification process takes place by mechanical stirring using a three-blade propeller or a hear shear rotor-stator homogenizer such as Ultra-Turrax available by IKA or an in-line homogenizer MT-3000 available by Kinematica.

The emulsion is then transferred to a sufficient amount of quench media (water or aqueous buffer) under continuous stirring, into which the solvent associated with the oily droplets is diffused out. The volume of quench media is on the order of 0.7-3 times the quench volume needed to dissolve completely all organic solvent contained in the inner and outer phase (saturated volume). Preferably the quench volume is from 0.8-fold to 2-fold the saturated volume. Further to extraction, solvent removal can be optionally facilitated through evaporation by heating to a temperature up to 40° C.

The particles are collected over 45-μm and 250-μm mesh size stainless steel sieves arranged in series. The fraction collected over the small sieve size is rinsed with water and finally dried under vacuum.

The inventors have unexpectedly discovered that the release profile of the final microparticles can be controlled either by adjusting the degree of saturation of the outer aqueous phase with the organic solvent used in the inner phase in combination with the appropriate temperature at quenching or by preparing an inner/oil phase of low polymer concentration and an outer aqueous phase saturated with the organic solvent in combination with the appropriate temperature at quenching. Particularly, if an oversaturated outer phase or a low polymer concentration inner/oil phase emulsified into a saturated outer phase is combined with a low temperature at quenching step (i.e., 5° C. or less) the release profile of the prepared microparticles will be substantially sigmoidal with an initial lag phase. The same can be achieved when a saturated outer phase is combined with a high temperature at quenching step (i.e., >30° C.). All other combinations including oversaturated outer phase with increased temperature at quench (i.e., T>5° C.) or saturated outer phase with high polymer concentration of inner/oil phase with a temperature lower than 30° C. at quench results in high early release and almost linear release profiles.

The inventors believe that the above process parameters are critical and define the density of the final microparticles and the distribution of the drug into the polymer matrix. Both quality properties impact the degradation rate and consequently the release characteristics of the prepared microparticles.

EXAMPLES

Example 1a & 1b

For the preparation 1a, 841.5 g of 1% poly(vinyl alcohol) solution (Polyvinyl alcohol 4-88 EMPROVE® exp, Merck Millipore) are mixed together with 61.2 g of dichloromethane, forming an oversaturated outer phase (OP).

For the preparation of the inner phase (IP), first, 8.1 g of high inherent viscosity (0.76 dl/g) 75:25 poly(D,L lactide-co-glycolide) (commercially available from Purac under the trade name PURASORB PDLG 7507), are dissolved in 81 g dichloromethane, forming a polymer solution of 10%

(w/w). Then, and after the complete dissolution of the polymer, 5.4 g of risperidone base are added to the polymer solution and mixed in order to get a clear solution. The two phases are combined together, by using a lab in-line homogenizer (MEGATRON® System MT 3000, Kinematica). The IP and OP are pumped simultaneously at 16.7 ml/min and 220 mL/min, respectively, into the in-line mixer which is set at 800 rpm. The outlet of the homogenizer is introduced directly into a quench media, composed of 8752 g of water for injection, 13.5 g of anhydrous sodium carbonate and 10.8 g of anhydrous sodium bicarbonate under vigorous stirring (1200 rpm) at a specific temperature (i.e., 5° C. or 20° C.).

After 5 hours of quenching, the formed dispersion is passed through a stainless steel sieve column composed of 45 and 250 µm mesh sizes sieves. The microparticles retained on the 45 µm sieve, are washed carefully with a solution of 2000 ml water for injection and 800 ml ethanol, in order to remove the risperidone base that has not been encapsulated. Finally, the final step consists of the collection and drying, for approximately 72 hours at 20° C. and at 10 mbar, of the produced microparticles.

Example 2a-2e 420.75 g of 1% poly(vinyl alcohol) solution (Polyvinyl alcohol 4-88 EMPROVE® exp, Merck Millipore) are mixed together with 5.47 g of dichloromethane, forming a saturated outer phase (OP).

For the preparation of the inner phase (IP), first, 4.05 g of high inherent viscosity (0.76 dl/g) 75:25 PLGA polymer (commercially available from Purac under the trade name PURASORB PDLG 7507), are dissolved in 40.5 g dichloromethane, forming a polymer solution of 10% (w/w). Then, and after the complete dissolution of the polymer, 2.7 g of risperidone base are added to the polymer solution and mixed in order to get a clear solution.

The two phases are combined together, by the slow addition of the DP in the CP under mechanical stirring at 1200 rpm (IKA overhead stirrer EUROSTAR 20). After 5 minutes of emulsification, the emulsion is transferred slowly into a quench media, composed of 3278.5 g of water for injection, 6.75 g of anhydrous sodium carbonate and 5.4 g of anhydrous sodium bicarbonate under vigorous stirring (1000 rpm) at 5°, 10°, 20°, 30° or 40° C.

After 5 hours of quenching, the formed dispersion is passed through a stainless steel sieve column composed of 45 and 250 µm mesh sizes sieves. The microparticles retained on the 45 µm sieve, are washed carefully with a solution of 2000 ml water for injection and 800 ml ethanol, in order to remove the risperidone base that has not been encapsulated.

Finally, the final step consists of the collection and drying, for approximately 72 hours at 20° C. and at 10 mbar, of the produced microparticles.

Example 3

640.0 g of 1% poly(vinyl alcohol) solution (Polyvinyl alcohol 4-88 EMPROVE® exp, Merck Millipore) are mixed together with 8.32 g of dichloromethane, forming a saturated outer phase (OP).

For the preparation of the inner phase (IP), first, 4.04 g of high inherent viscosity (0.76 dl/g) 75:25 PLGA polymer (commercially available from Purac under the trade name PURASORB PDLG 7507), are dissolved in 57.77 g dichloromethane, forming a polymer solution of 7% (w/w). Then, and after the complete dissolution of the polymer, 2.7 g of risperidone base are added to the polymer solution and mixed in order to get a clear solution.

The two phases are combined together, by using a lab in-line homogenizer (MEGATRON® System MT 3000, Kinematica). The IP and OP are pumped simultaneously at 16.67 ml/min and 220 mL/min, respectively, into the in-line mixer which is set at 800 rpm. The outlet of the homogenizer is introduced directly into a quench media, composed of 3300 g of water for injection, 6.79 g of anhydrous sodium carbonate and 5.44 g of anhydrous sodium bicarbonate under vigorous stirring (1200 rpm) at a specific temperature (i.e., 5° C.).

After 5 hours of quenching, the formed dispersion is passed through a stainless steel sieve column composed of 45 and 250 µm mesh sizes sieves. The microparticles retained on the 45 µm sieve, are washed carefully with a solution of 2000 ml water for injection and 800 ml ethanol, in order to remove the risperidone base that has not been encapsulated. Finally, the final step consists of the collection and drying, for approximately 72 hours at 20° C. and at 10 mbar, of the produced microparticles.

Particle Size Distribution (PSD) Analysis

Particle size distribution was measured by laser diffraction using a Malvern Master Sizer 2000 Hydro2000S. The average particle size is expressed as the volume mean diameter in microns.

Drug Loading Analysis 25 mg of micorparticle containing risperidone are added in 50 ml acetonitrile and subjected to sonication for 10 min to facilitate dissolution. The solution is then filtrated through PTFE hydrophilic 0.45 µm syringe filter. Risperidone loading is assessed using reverse-phase HPLC Shimadzu equipment under the following conditions: column, XTerra RP18 µm, 4.6×150 mm; mobile phase, 45/55 acetonitrile/phosphate buffer pH 7.8; column temperature, 30° C.; flow rate, 1 mL/min; injection volume, 10 µL; detection, UV 278 nm; run time, 8 min. The calibration standard curve ranges from 20 to 240 µg/mL of risperidone dissolved in acetonitrile. The drug loading is expressed as % weight with respect to microparticle.

Mean Molecular Weight Measurement

The molecular weight of microparticles was determined by gel permeation chromatography (GPC) using an Agilent Model GPC 50Plus system equipped with 2 columns PLgel 5 µm Mixed-D 300×7.5 mm connected in series and a refractive index (RI) detector. The mobile phase is THF with a flow rate of 1 ml/min and the temperature of the column is 30° C. For the analysis of the samples, 10-15 mg of microparticles are dissolved in 5 mL THF and the solution is left overnight under stirring. 2 ml are withdrawn, filtered through a 40 µm PTFE filters and analyzed. The injection volume is 100 µL. The data collection and analysis was performed using Cirrus software. Polystyrene standards with MW range between 162 and 371100 are used for calibration.

API-Depletion Index

For the measurement of the API-depletion index, mid-infrared spectroscopy was performed on the dry powder of the microspheres in the Attenuated Total Reflection (ATR) mode over the wavenumber range from 550 to 4000 cm-1 at a resolution of 4 cm-1. Each spectrum is the average of 100 scans. A Fourier transform instrument was used (Equinox 55 by Bruker Optics) equipped with a single 45° reflection diamond ATR accessory (DuraSampl IR2 by SensIR). The penetration (hence, sampling) depth of this technique is of the order of 5 µm. The Absorbance spectra were corrected for the k-dependence of the penetration depth and shown in the so-called ATR absorbance formalism. An empirical indicator comparing the integrated intensity of the polymer matrix band (1850-1680 cm-1) to the API-related bands in the 1680-1505 cm-1 range, has been developed to provide a semiquantitative estimate of surface depletion phenomena.

In Vitro Release Method

In vitro release studies were perfumed in a USP-II apparatus (Distek dissolution apparatus) using as release media 1000 ml of saline Buffer pH 7.4 containing 0.03% sodium azide. The temperature is controlled at 37° C. and the paddle speed is set at 100 rpm. An appropriate amount of particles containing 24 mg of risperidone drug substance are transferred into the vessels ensuring sink conditions (risperidone solubility in phosphate buffer pH 7.4 is 0.22 mg/ml). Sampling is performed at specified time intervals from 24 hrs to 960 hrs and the % drug release is measured by RP-HPLC analysis to withdrawn samples using the same conditions as for the drug loading measurements.

| Trial No | OP saturation degree | Quench Temperature | PSD in μm D(0.1):D(0.5):D(0.9) | % Drug Loading | MW | In vitro release 20d-30d-34d | Depletion Index |
|---|---|---|---|---|---|---|---|
| 1a | Oversaturated | 5 | 41.9:68.8:110.0 | 36.57 | 112854 | 3.3:40.7:98 | 20 |
| 1b | | 20 | 46.6:63.5:87.1 | 32.69 | 104504 | 20.2:71.2:88.7 | 13 |
| 2a | Saturated | 5 | 83.2:126.2:187.9 | 36.28 | 99245 | 28:80.9:90.9 | 6 |
| 2b | | 10 | 75.0:118.2:184.2 | 35.94 | 98234 | 27.1:81.8:97.8 | 7 |
| 2c | | 20 | 85.0:135.5:206.0 | 35.56 | 99490 | 21.8:86.5:99.4 | 12 |
| 2d | | 30 | 54.4:85.1:136.2 | 34.16 | 94350 | 14.4:76.1:93.3 | 14 |
| 2e | | 40 | 58.8:83.5:118.1 | 34.43 | 69724 | 5.65:84.5:89.9 | 21 |
| 3 | Saturated | 5 | 41.9:71.97:116.3 | 36.0 | 113947 | 2.88:39.4:88.1 | 26 |

The invention claimed is:

1. A process for the preparation of biodegradable microparticles of poly(D,L lactide-co-glycolide) (PLGA) polymer, having a sigmoidal release profile of Risperidone, contained within the microparticles, comprising:
   a. preparing an inner oil phase by dissolving the PLGA polymer and Risperidone in an organic solvent, wherein the polymer concentration in the inner oil phase is in the range of 5-8% wt;
   b. preparing an outer aqueous phase comprising of water, polyvinyl alcohol (PVA), optionally an aqueous buffer solution to adjust the pH to a value that Risperidone appears the lower solubility, and the same organic solvent used in the inner oil phase, wherein the amount of organic solvent added in the outer phase is sufficient to saturate the outer phase;
   c. emulsifying the inner phase into the outer phase either by mechanical stirring or using a high shear homogenizer;
   d. transferring the emulsion into a quench media having a temperature set at 5° C. and being thermostatically controlled thermostatically controlled thereby forming a dispersion;
   e. separating hardened microparticles from the dispersion and, optionally washing of the hardened microparticles; and
   f. drying the hardened microparticles in a single drying step with no further washing and/or drying step; and
   g. wherein the combination of the polymer concentration in the inner oil phase in the range of 5-8% wt in step (a), the saturated outer phase of step (b), and the quench media temperature of 5° C. in step (d) results in microparticles having a sigmoidal release profile of Risperidone, without any additional drying and/or washing steps as cited in step (f).

2. The process according to claim 1, wherein the volume of the quench media is controlled from 0.7 to 3 times of the volume needed to dissolve all of organic solvent.

3. The process according to claim 1, wherein sigmoidal release is an vitro release profile characterized by an initial lag phase, a steep intermediate release phase, and a flat final release phase as determined in a USP-II apparatus using as release media 1000 ml of saline buffer pH 7.4 containing 0.03% sodium azide and the temperature is controlled at 37° C. and the paddle speed is set at 100 rpm.

4. The process according to claim 1, wherein sigmoidal release corresponds to less than 10% drug released in 20 days, 35-80% in 30 days and more than 80% up to day 34 when dissolution is determined in a USP-II apparatus using as release media 1000 ml of saline buffer pH 7.4 containing 0.03% sodium azide and the temperature is controlled at 37° C. and the paddle speed is set at 100 rpm.

5. A process for the preparation of biodegradable microparticles of poly(D,L lactide-co-glycolide) (PLGA) polymer, having a sigmoidal release profile of Risperidone, contained within the microparticles, comprising:
   a. preparing an inner oil phase having a viscosity of 10-1000 cP by dissolving PLGA polymer and Risperidone in an organic solvent, wherein the polymer concentration in the inner oil phase is in the range of 5-40% wt;
   b. preparing an outer aqueous phase comprising of water, polyvinyl alcohol (PVA), optionally an aqueous buffer solution to adjust the pH to a value that Risperidone appears the lower solubility, and the same organic solvent used in the inner oil phase, wherein the amount of organic solvent added in the outer phase is sufficient to saturate the outer phase;
   c. emulsifying the inner phase into the outer phase either by mechanical stirring or using a high shear homogenizer;
   d. transferring the emulsion into a quench media having a temperature set in the range of 30-40° C. and being thermostatically controlled thermostatically controlled thereby forming a dispersion;
   e. separating hardened microparticles from the dispersion and, optionally washing of the hardened microparticles; and
   f. drying the hardened microparticles in a single drying step with no further washing and/or drying step;
   g. wherein the combination of the saturated outer phase in step (b) and the quench media temperature in the range of 30-40° C. in step (d) results in microparticles having a sigmoidal release profile of Risperidone, without any additional dying and/or washing steps as cited in step (f).

6. The process according to claim 5, wherein the concentration of PLGA polymer is 5-15% providing a solution viscosity of 10-100 cP.

7. A process for the preparation of biodegradable microparticles of poly(D,L lactide-co-glycolide) (PLGA)

polymer, having a sigmoidal release profile of Risperidone, contained within the microparticles, comprising:
- a. preparing an inner oil phase having a viscosity of 10-1000 cP by dissolving PLGA polymer and Risperidone in an organic solvent, wherein the polymer concentration in the inner oil phase is in the range of 5-40% wt;
- b. preparing an outer aqueous phase comprising of water, polyvinyl alcohol (PVA), optionally an aqueous buffer solution to adjust the pH to a value that Risperidone appears the lower solubility, and the same organic solvent used in the inner oil phase, wherein the amount of organic solvent is added in an amount 2-10 times above a saturation point of the outer phase, thereby forming an oversaturated outer phase;
- c. emulsifying the inner phase into the outer phase either by mechanical stirring or using a high shear homogenizer;
- d. transferring the emulsion into a quench media having a temperature set at 5° C. and being thermostatically controlled thermostatically controlled thereby forming a dispersion;
- e. separating hardened microparticles from the dispersion and, optionally washing of the hardened microparticles, and
- f. drying the hardened microparticles in a single drying step with no further washing and/or drying step; and
- g. wherein the combination of the oversaturated outer phase in step (b) and the quench media temperature of 5° C. in step (d) results in microparticles having a sigmoidal release profile of Risperidone, without any additional drying and/or washing steps as cited in step (f).

8. The process according to claim 7, wherein the concentration of PLGA polymer is 5-15% providing a solution viscosity of 10-100 cP.

9. The process according to claim 7, wherein the amount of organic solvent in the inner oil phase is 4 to 6 times the amount of the solvent that can be dissolved in the volume of the aqueous phase.

* * * * *